United States Patent [19]

Morita

[11] Patent Number: 4,474,771
[45] Date of Patent: Oct. 2, 1984

[54] HIGH-MOLECULAR-WEIGHT SUBSTANCE HAVING DESMUTAGENIC ACTIVITY EXTRACTED FROM THE ROOT OF BURDOCK, AND PROCESS FOR SEPARATING AND PURIFYING SAID SUBSTANCE

[75] Inventor: Kazuyoshi Morita, Odawara, Japan
[73] Assignee: Kanebo Ltd., Tokyo, Japan
[21] Appl. No.: 371,489
[22] Filed: Apr. 23, 1982

Related U.S. Application Data

[63] Continuation-in-part of Ser. No. 285,184, Jul. 13, 1981, abandoned.

[30] Foreign Application Priority Data

Nov. 26, 1979 [JP] Japan .................................. 54-153267

[51] Int. Cl.$^3$ ............................................. A61K 35/78
[52] U.S. Cl. ..................................................... 424/195
[58] Field of Search .................................. 424/195, 10

[56] References Cited

FOREIGN PATENT DOCUMENTS 122715 9/1979 Japan .

OTHER PUBLICATIONS

Agricultural Biol. Chem. (Japan), 42:1235–1238, 1978.
The Dispensatory of the USA, 24th ed., p. 1500, 1947.
TAMA, May 1978, vol. 239, No. 20 p. 2157.

*Primary Examiner*—Jerome D. Goldberg
*Assistant Examiner*—John W. Rollins
*Attorney, Agent, or Firm*—Wenderoth, Lind & Ponack

[57] ABSTRACT

A high-molecular-weight substance extracted from the root of edible burdock, characterized in that (1) said substance is soluble in water and alkaline aqueous solutions,
(2) said substance is adsorbable to an anion exchange cellulose but not adsorbable to a cation exchange cellulose,
(3) said substance has an absorption wavelength peak within a range of 280 nm to 300 nm, and
(4) said substance has a desmutagenicity such that when the number of revertant colonies from Salmonella TA98 is determined by using 2-nitro-p-phenylenediamine as a mutagen in accordance with the inhibitory effect test described in the specification, the concentration of the high-molecular-weight substance at which the desmutagenic rate (%) becomes 50% is 4 to 6 parts by weight per part by weight of the 2-nitro-p-phenylenediamine.

The high-molecular-weight substance may be prepared by a process which comprises the steps of:
(a) centrifuging the juice of burdock to remove foreign materials therefrom,
(b) mixing the resulting supernatant with a phosphate buffer having a concentration of 1 to 2 moles and a pH of about 6.5 to about 7.5, salting out the mixture with a water-soluble alkali metal or ammonium salt of an inorganic acid, and thereafter collecting the precipitate,
(c) dissolving the precipitate in a phosphate buffer having a concentration of about 10 to about 400 mM and a pH of about 6.5 to about 7.5, and dialyzing the resulting solution, and
(d) ultrafiltering the dialyzate and withdrawing the concentrate and as required, lyophilizing the concentrate to yield a powder.

The high-molecular-weight substance is useful for preventing the induction of mutation in an animal by a mutagen.

6 Claims, 2 Drawing Figures

HIGH-MOLECULAR-WEIGHT SUBSTANCE HAVING DESMUTAGENIC ACTIVITY EXTRACTED FROM THE ROOT OF BURDOCK, AND PROCESS FOR SEPARATING AND PURIFYING SAID SUBSTANCE

This application is a continuation-in-part application of Ser. No. 285,184 filed on July 13, 1981, now abandoned.

FIELD OF INVENTION

This invention relates to a high-molecular-weight substance extracted from the root of edible burdock and having the ability to inhibit the mutagenicity of mutagens, and to a process for separating and purifying it.

DESCRIPTION OF PRIOR ART

It has recently been known that most carcinogenous substances show mutagenicity and there is every possibility that a mutagen is a carcinogen. It is reported that some substances encountered in our daily life, for example AF-2 (2-(2-furyl)-3-(5-nitro-2-furyl)acrylamide), Trp-P-1(3-amino-1,4-dimethyl-5H-pyrido[4,3-b]indole) and Trp-P-2(3-amino-1-methyl-5H-pyrido[4,3-b]indole), the latter two being present in the scorched portions of roasted or grilled meat and fish, exhibit mutagenicity and induce carcinogenicity in animals.

The present inventor, in association with others, previously suggested a process for separating a desmutagenic factor in pure form from cabbage juice obtained by mechanically crushing cabbage followed by filtration (see Japanese Laid-Open Patent Publication No. 122715/1979 and U.S. Pat. No. 4,191,752). This process involves the steps of (1) centrifuging the juice of cabbage, (2) ultracentrifuging the resulting supernatant, (3) contacting the supernatant with an anion exchange cellulose, (4) applying the unadsorbed fraction to a column of a cation exchange cellulose, (5) collecting the active fraction eluted at low salt concentrations, and (6) charging the active fraction onto a molecular sieve for purification. The final fraction thus obtained is a hemoprotein which has a characteristic absorption spectrum at 280 nm and 404 nm, is stable to heat, and has the property of being deactivated by proteolytic enzymes. It was observed that this desmutagenic factor separated from cabbage juice inhibits the mutagenicity of various mutagens which manifest their mutagenicity when metabolized, for example Trp-P-1(3-amino-1,4-dimethyl-5H-pyrido[4,3-b]indole), Trp-P-2(3-amino-1-methyl-5H-pyrido[4,3-b]indole), N-butyl-N-acetoxynitrosamine, the reaction products of sorbic acid with nitrites, 2-aminoanthracene, ethidium bromide, and pyrolyzates of amino acids such as tryptophan and ornithine.

The final fraction from the cabbage juice, however, has the defect that it is deactivated in the presence of proteolytic enzymes, and cannot inhibit, but rather enhances greatly, the mutagenicity of mutagens which manifest their mutagenicity without metabolism, such as hair-dyeing nitroaminobenzene-type dyes (e.g., 4-nitro-o-phenylenediamine and 2-nitro-p-phenylenediamine).

The present inventor previously reported in Agric. Biol. Chem., 42 (6), pages 1235–1238, 1978 from a qualitative viewpoint that supernatant liquids obtained by centrifuging the juices of cabbage, broccoli, green pepper, eggplant, apple, burdock, shallot, ginger, pineapple and mint leaf inhibit the mutagenicity of tryptophan pyrolyzates.

While these vegetables and fruits exhibit the activity of inhibiting the mutagenicity of substances which manifest their mutagenicity when metabolized, further investigations of the present inventor have shown that among them, only an active fraction in pure form obtained from burdock exhibits an excellent and very specific activity of inhibiting the mutagenicity of substances which manifest their mutagenicity without metabolism, such as nitroaminobenzene-type dyes.

Only the burdock juice among them can inhibit the mutagenicity of hair-dying nitroaminobenzene dyes such as 2-nitro-p-phenylenediamine and 4-nitro-o-phenylenediamine which manifest their mutagenicity without being metabolized although its inhibiting activity is low and not entirely satisfactory. On the other hand, the burdock juice markedly increases the mutagenicity of such hair-dying nitroaminobenzene dyes as 2-nitro-4-aminophenol and 2-amino-5-nitrophenol (Example 2 given hereinafter shows a comparison of the high-molecular-weight substance in accordance with this invention with the burdock juice). Although it has not been fully known why the burdock juice enhances mutagenicity in this way, it is presumed that certain components (impurities) contained in the burdock juice may be responsible for it.

Investigations of the present inventor have also shown that water-soluble substances obtained from the juices of garland chrysanthemum (*Chrysanthemum coronarium* Linn.), coltsfoot (*Petasites japonicus* MIQ.), and lettuce, which are plants belonging to the family Compositae as does burdock, in the same way as in the preparation of the burdock juice, do not show an activity of inhibiting the mutagenicity of substances which manifest their mutagenicity without metabolism, for example hair-dyeing nitroaminobenzene-type dyes.

Furthermore, the above-cited literature reference only discloses supernatant liquids obtained by centrifugation of vegetable and fruit juices, and neither describes nor suggests methods for separating active components from the supernatant liquids and purifying them, and therefore fails to suggest anything about the active components in the purified state.

SUMMARY OF THE INVENTION

It is an object of this invention therefore to provide a desmutagenic high-molecular-weight substance separated in pure form from the root of edible burdock.

Another object of this invention is to provide a high-molecular-weight substance in pure form separated from the root of edible burdock, which has the activity of inhibiting the mutagenicity of substances which manifest their mutagenicity without being metabolized.

Still another object of this invention is to provide said high-molecular-weight substance in pure form which does not substantially decrease in its activity of inhibiting mutagenicity even when treated at elevated temperatures.

A further object of this invention is to provide a process for efficiently separating said high-molecular-weight substance from the root of edible burdock and recovering it in pure form.

Other objects and advantages of this invention will become apparent from the following description.

These objects and advantages are achieved in accordance with this invention by a high-molecular-weight substance extracted from the root of edible burdock, characterized in that (1) said substance is soluble in water and alkaline aqueous solutions, (2) said substance is adsorbable to an anion exchange cellulose but not adsorbable to a cation exchange cellulose, (3) said substance has an absorption wavelength peak within a range of 280 nm to 300 nm, and (4) said substance has a desmutagenicity such that when the number of revertant colonies from Salmonella TA98 is determined by using 2-nitro-p-phenylenediamine as a mutagen in accordance with the inhibitory effect test described below, the concentration of the high-molecular-weight substance at which the desmutagenic rate (%) defined by the following equation $$DR(\%) = \frac{(a - c) - (b - c)}{a - c} \times 100$$

wherein a is the number of revertant colonies in the absence of the high-molecular-weight substance, b is the number of revertant colonies in the presence of the high-molecular-weight substance, and c is the number of spontaneous revertant colonies, becomes 50% is 4 to 6 parts by weight per part by weight of the 2-nitro-p-phenylenediamine.

The high-molecular-weight substance provided by this invention can be separated from the root of burdock and recovered in pure form by a process comprising the steps of:

(a) centrifuging the juice of burdock to remove foreign materials therefrom, (b) mixing the resulting supernatant with a phosphate buffer having a concentration of 1 to 2M and a pH of about 6.5 to about 7.5, salting out the mixture with a water-soluble alkali metal or ammonium salt of an inorganic acid, and thereafter collecting the precipitate, (c) dissolving the precipitate in a phosphate buffer having a concentration of about 10 to about 400 mM, and a pH of about 6.5 to about 7.5 and dialyzing the resulting solution, and (d) ultrafiltering the dialyzate and withdrawing the concentrate, and a required, lyophilizing the concentrate to yield a powder.

DETAILED DESCRIPTION OF THE INVENTION

Figure 1:
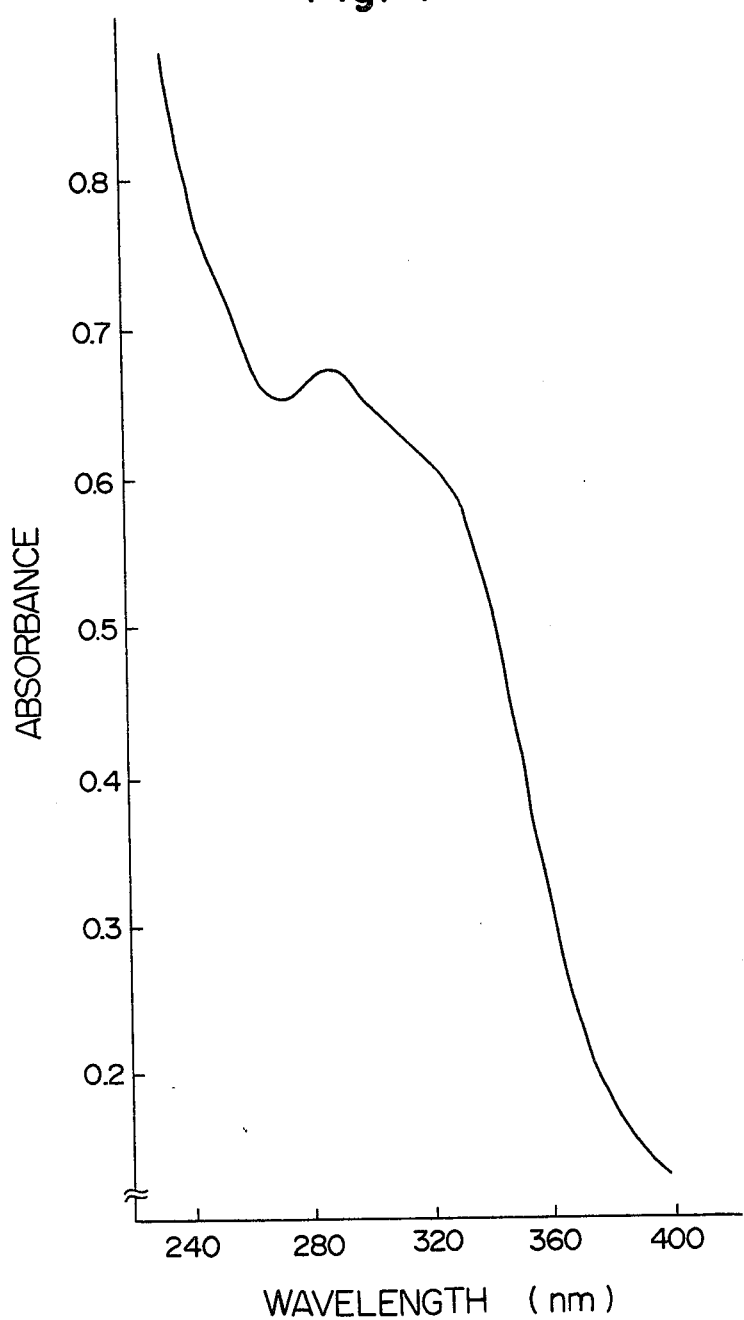
FIG. 1 and FIG. 2 represent, respectively, the ultraviolet absorption curve and elution curve of the high-molecular-weight substance of the present invention.

Burdock, as used herein, is *Arctium Lappa Linne* or *Lappa edulis* SIEB. belonging to the genus Arctium of the family Compositae, and its root is edible.

The root of burdock from which the aforesaid high-molecular-weight substance is to be extracted in pure form by this invention may be harvested within three years after sowing which is done either in spring or fall. Preferably, it is the root of burdock sown in spring and harvested in winter the same year, or that sown in fall and harvested in spring the next year. The harvested roots may be used raw or after drying.

It has been found in accordance with this invention that the desmutagenic activity of the high-molecular-weight substance extracted from burdock by this invention does not substantially decrease even when it is treated at elevated temperatures, for example at about 100° C. for 15 minutes. Another characteristic feature of the high-molecular-weight substance of the invention is that its desmutagenic activity is markedly decreased by a manganese ion, but is not substantially decreased by a magnesium or calcium ion.

In extracting the desmutagenic substance in pure form from the root of burdock by the process of this invention, the juice of burdock is centrifuged to remove foreign materials therefrom if they are present.

The burdock juice can be produced by washing the root of raw burdock with water and crushing the root in a juicer to remove most of the fibrous matter and obtain the product as an aqueous solution or suspension; or by suspending a dry powder of the root of burdock in water or a phosphate buffer (pH about 6.5 to about 7.5), for a sufficient period of time, optionally at elevated temperatures, removing most of the fibrous matter, and recovering the product as an aqueous solution or suspension.

The dried powder of burdock root should be as fine as possible. Preferably, such a powder is ground by a triturator usually at about 20° to about 85° C. for about 2 to 24 hours to extract the burdock juice as an aqueous solution or suspension.

When the burdock juice contains foreign materials, it is centrifuged to remove them. Centrifugation may be usual centrifugation performed at 7000 to 15,000 G or ultracentrifugation performed at 100,000 to 200,000 G. Or it may be first subjected to usual centrifugation and then to ultracentrifugation.

The usual centrifugation is normally carried out for 30 to 60 minutes to remove the fibrous matter, chloroplast, mitochondria, etc. in the juice. The ultracentrifugation is preferably carried out usually for 1 to 2 hours to remove the microsome, ribosome, etc.

A phosphate buffer (pH about 6.5 to about 7.5) is added to the supernatant left after the removal of the foreign materials from the burdock juice as above. When the juice has been produced by suspending the burdock powder in a phosphate buffer as above, it is not always necessary to add additional phosphate buffer. It should be understood that the latter case also falls within the scope of the present invention.

It is preferred that the phosphate buffer to be added to the burdock juice usually have a pH of about 6.5 to about 7.5. Usually, it consists of monosodium or monopotassium phosphate and disodium or dipotassium phosphate, preferably monopotassium phosphate and dipotassium phosphate. Conveniently, the phosphate buffer usually has a concentration of about 1 to 2 moles. Preferably, the phosphate buffer is added in an amount 1/20 to 1/100 times the volume of the supernatant. Furthermore, the phosphate buffer should preferably be added such that the phosphate ion concentration in the supernatant to which the phosphate buffer has been added reaches about 10 to about 400 mM.

For salting out, a water-soluble alkali metal or ammonium salt of an inorganic acid is added to the resulting solution. Examples of the inorganic acid are carbonic acid, sulfuric acid, hydrochloric acid and phosphoric acid, and examples of preferred alkali metal or ammonium salts of these inorganic acids are potassium carbonate, ammonium sulfate, sodium sulfate and potassium phosphate.

The amount of the water-soluble alkali metal or ammonium salt of the inorganic acid to be used is preferably about 30 to about 80% by weight based on the aforesaid mixture of the supernatant and the phosphate buffer.

From the resulting solution containing a precipitate, the precipitate is separated by various means such as filtration or centrifugation. Filtration may be carried out at atmospheric, reduced or elevated pressures. Desirably, the separation is effected by centrifugation. The centrifugation is usually carried out under the aforesaid conditions by the so-called "usual centrifugation".

The precipitate so separated is then dissolved in a phosphate buffer (about 10 to about 400 mM; pH 6.5 to 7.5), and the solution is dialyzed. Usually, the amount of the phosphate buffer used is about 5 to about 10 ml per gram of the precipitate. Dialysis can be carried out by using water, a phosphate buffer, etc. Usually, it is preferred to employ the phosphate buffer. A cellulose membrane or a cellophane membrane for artificial kidneys may be used as a dialysis membrane.

The dialyzate left after removal of low-molecular-weight substances by the dialysis is then ultrafiltered to concentrate it. Desirably, the ultrafiltration is continued until the volume of the dialyzate reaches ⅓ to 1/5 of the original volume. For example, filters available under the trade names PM-30, XM-50, XM-100 and XM-300 (made in Amicon Far East Ltd.) can be used in the ultrafiltration. XM-300 which is an ultrafiltration membrane permitting passage of molecules having a molecular weight of less than about 300,000 is especially preferred.

The concentrate obtained as a result of the ultrafiltration constitutes the high-molecular-weight substance of the invention. According to this invention, the concentrate may, as required, be lyophilized in a usual manner to form a powder.

When the concentrate contains the phosphate buffer, it is preferred to add water to the concentrate in an amount about 3 to about 5 times the volume of the latter, and again ultrafilter the mixture.

The high-molecular-weight substance extracted from the root of edible burdock by the process of this invention has been found to have sufficient desmutagenicity as demonstrated by its desmutagenic rate measured by the inhibitory effect test to be described hereinafter.

According to the process of this invention, the high-molecular-weight substance can be obtained in a higher purity by partly modifying the above-described process. One such modification is a procedure of treating the dialyzate with a cation exchanger before the ultrafiltration step and then subjecting the treated dialyzate to the ultrafiltration step. Since the high-molecular-weight substance of the invention is not adsorbable to a cation exchanger, this procedure results in removal of impurities which can be adsorbed to the cation exchanger. Useful cation exchangers for this purpose are cellulose and dextran type exchangers containing a carboxyl group, a sulfonic acid group, a phosphoric acid group, etc. as cation exchange group, such as CM-Cellulose, P-Cellulose, CM-Sephadex, SP-Sephadex and CM-Cepharose (manufactured by Farmacia Fine Chemicals, or Watman Company).

Another modification of the process of this invention is a procedure of diluting the concentrate obtained by the ultrafiltration (irrespective of whether it is treated with a cation exchanger before the ultrafiltration) with a phosphate buffer (about 10 to about 400 mM; pH about 6.5 to 7.5), and again ultrafiltering the diluted concentrate. Preferably, this additional ultrafiltration is carried out two or three times, and every time, the concentrate is concentrated to ⅓ to 1/5 the original volume and diluted with a phosphate buffer to the original volume before the next ultrafiltration. By the additional ultrafiltration, considerable amounts of impurities ranging from low-molecular-weight substances to substances having a considerably high-molecular-weight (less than about 300,000) can be removed.

When this additional ultrafiltration is practiced, the final concentrate obtained should be dialyzed against water. This results in the formation of the high-molecular-weight substance of this invention as a solution free from a phosphate salt.

Still another modification of the process of this invention is a procedure of precipitating the high-molecular-weight substance of this invention by treating the concentrate obtained by the above ultrafiltration or the additional ultrafiltration with trichloroacetic acid. By separating the precipitate, impurities, mainly those derived from sugars, can be removed from the concentrate. The separated precipitate is then suspended in water and dialyzed against water to remove trichloroacetic acid therefrom, thus giving the high-molecular-weight substance of this invention in a highly pure state. In this procedure, trichloroacetic acid can be used in a proportion of 1 to 10 g per 100 cc of the concentrate to which it is added. The separation of the resulting precipitate can be performed, for example, by centrifugation and filtration.

According to the invention, the high-molecular-weight substance can be obtained in a very high purity by practicing the process comprising the steps (a) to (d) in combination with one or more of these three modifications. The high-molecular-weight substance produced by modifying the process of this invention as above has the property of dissolving in an alkaline aqueous solution more easily than in water.

The high-molecular-weight substance provided by this invention, which is in the form of a concentrate or a powder and in a highly purified state, is administered to man or other animals either as such or in combination with suitable pharmaceutically acceptable carriers or adjuvants.

Accordingly, the present invention also provides a pharmaceutical composition comprising the high-molecular-weight substance together with a pharmaceutically acceptable carrier or adjuvant, or a drug composed of the above pharmaceutical composition.

Examples of the carrier or adjuvant include excipients (e.g., starches such as corn starch and potato starch, sugars such as lactose and sucrose, and inorganic salts such as calcium sulfate and calcium phosphate), lubricants (e.g., magnesium stearate and talc), disintegrants (e.g., carboxymethyl cellulose, cellulose, and agar), and encapsulating agents (e.g., gelatin) which are usually known to those skilled in the art.

The form of the drug may, for example, be tablets, granules, sugar-coated tablets, powders, syrups, solutions, and capsules.

Preferably, the high-molecular-weight substance of the invention in the above forms is administered orally. It can also be used for external application (application to the skin), preferably in the form of ointments such as those consisting of an oil-soluble base (e.g., wax), aqueous emulsions, aqueous solutions, etc.

According to this invention, there is also provided a method for preventing the induction of mutation in an animal by a mutagen, which comprises administering an amount, effective for preventing the occurrence of mutation, of the high-molecular-weight substance of the invention either singly or in the form of the aforesaid composition or drug to an animal which is expected to take, or has taken, the mutagen. The dosage can be properly determined by a specialist such as a physician or a pharmacist according to the animal to which the above substance is to be administered. Usually, it is about 100 mg to about 2.5 g per kilogram of body weight per day.

Since the high-molecular-weight substance of this invention is a component of the root of burdock which is eaten as a food, it gives rise to no toxicity problem.

The taking of the mutagen by an animal means not only its taking into the body of the animal, but also the contacting of the animal with the mutagen.

The high-molecular-weight substance of this invention exhibits an excellent action in preventing mutation caused not only by substances (mutagens) which manifest mutagenicity without being metabolized but also by substances (mutagens) which manifest mutagenicity after undergoing metabolism. In particular, the high-molecular-weight substance of the invention is unique in that it exhibits an excellent inhibitory effect against substances which manifest mutagenicity without metabolism, and this behavior is quite different from the burdock juice which is derived likewise from the root of burdock.

Examples of the substances which manifest mutagenicity without being metabolized include 2-nitro-p-phenylenediamine, 4-nitro-o-phenylenediamine, 2-amino-4-nitrophenol, 2-amino-5-nitrophenol, and their salts such as the sulfates. On the other hand, examples of the substances which manifest mutagenicity after undergoing metabolism are p-phenylenediamine, o-phenylenediamine, 2,4-diaminoanisole, and their salts such as the sulfates.

The high-molecular-weight substance of the invention obtained by lyophilization is a brown powder which is stable, odorless, and soluble in water or alkaline aqueous solutions and has especially good storage stability. It is convenient to formulate into drugs of any form.

It is believed as a result of the present inventor's investigations that the desmutagenic activity of the high-molecular-weight substance is manifested in such a way that it inhibits the mutagenicity of a mutagen by directly acting on the mutagen. Desirably, therefore, the high-molecular-weight substance is administered preventively to an animal which is likely to take, or has taken, mutagens so as to inhibit manifestation of their mutagenicity.

The following Examples are given to illustrate in greater detail the process for separating and purifying the high-molecular-weight substance of the invention, and the desmutagenic activity and other properties of the high-molecular-weight substance of the invention.

EXAMPLE 1

(1) Separation of the active high-molecular-weight substance and its purification:

Five thousand grams of the root of burdock harvested in winter were washed with water, and crushed by a juicer (Toshiba JC-5404 manufactured by Toshiba Co.) to obtain about 3400 ml of a burdock juice. 3400 ml of the juice was centrifuged at 9000 G to obtain 2200 ml of a clear brown supernatant.

The supernatant was then mixed with a 1M phosphate buffer (pH 6.8; consisting of dipotassium phosphate and monopotassium phosphate; all phosphate buffers described hereinbelow consisted of the same ingredients) in an amount 1/20 the volume of the supernatant. Then, 1100 ml of the resulting mixture was salted out with 80%, based on the weight of the mixture, of ammonium sulfate. The salted-out mixture was centrifuged at 9000 G for 15 minutes to obtain 80 g of a precipitate.

A portion (60 g) of this precipitate was dissolved in a 50 mM phosphate buffer (pH 6.8) so as to provide 600 ml of a solution. The solution was dialyzed at 4° C. against the aforesaid phosphate buffer (pH 6.8) to obtain 696 ml of a dialyzate.

A portion (464 ml) of the dialyzate was ultrafiltered on a membrane filter XM-3000 (manufactured by Amicon Far East Ltd.) to concentrate it to $\frac{1}{3}$ its original volume. A 50 mM phosphate buffer (pH 6.8) was added to the concentrate to adjust its total amount to 200 ml. The mixture was again concentrated by ultrafiltration on the same filter as above to obtain 140 ml of a concentrate.

A portion (70 ml) of the concentrate was lyophilized at $-54°$ C. for 24 hours by a lyophilizer (Model FDX-1-54 manufactured by Central Science Co., Ltd.) to obtain 450 mg of a dry powder of a high-molecular-weight substance.

(2) Ultraviolet absorption characteristics of the active high-molecular-weight substance:

The ultraviolet absorption curve of the high-molecular-weight substance determined for an aqueous solution of its lyophilized powder is shown in FIG. 1 in which the ordinate represents the absorbance and the abscissa, the wavelength (nm). It is seen from FIG. 1 that the active high-molecular-weight substance has an absorption wavelength peak in the range of 280 nm to 300 nm (maximum wavelength about 290 nm).

(3) Adsorbability of the active high-molecular-weight substance to an anion exchange resin and a cation exchange resin:

27 ml of the concentrate obtained by the procedure shown in (1) above was charged onto a chromatographic column of DEAE-Cellulose (anion exchange cellulose) under the following conditions: the columnn size 2.5×12 cm, the elution speed 36 m/hr, the amount of elution 10 ml/test tube. The adsorbability of the active substance was examined by eluting the column with a 50 mM phosphate buffer having dissolved therein potassium chloride with a concentration gradient ranging from 50 mM to 2M. It was found that none of the fractions which were eluted without being adsorbed to the DEAE-Cellulose column showed desmutagenic activity.

Figure 2:
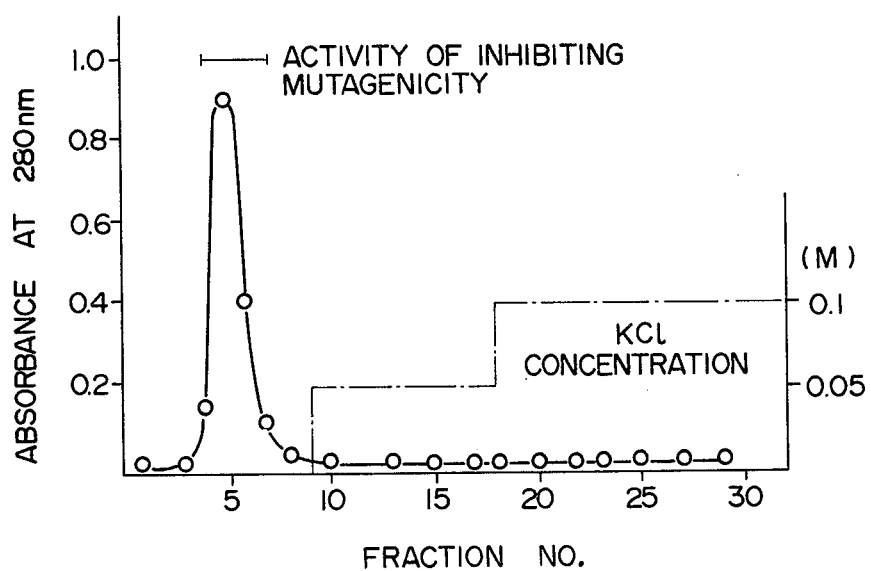

Similarly, 7 ml of the aforesaid concentrate was charged onto a chromatographic column of CM-Cellulose (cation exchange cellulose) under the following conditions: the column size 2.5×7 cm, the elution speed 40 ml/hr, the amount of elution 5.8 ml/test tube. The adsorbability of the active substance was examined by eluting the column with a 50 mM phosphate buffer having dissolved therein potassium chloride with a concentration gradient ranging from 50 mM to 0.1M. It was found that the concentrate was not adsorbed to the CM-Cellulose column, but eluted entirely. The elution curve is shown in FIG. 2 of the accompanying drawings.

The eluted fractions were subjected to the inhibitory effect test to be described hereinbelow, and found to have a desmutagenic rate of 88%. This desmutagenic rate substantially agreed with the desmutagenic rate (87.4%) of an aqueous solution of the dry powder shown in Table 2 (containing 1 mg/ml of the dry powder) whose amount was 500 μl/plate.

It was observed from the results of the desmutagenic test, too, that the active high-molecular-weight substance of this invention is a polyelectrolyte having a strongly anionic group.

(4) Inhibitory effects of the active high-molecular-weight substance:

(a) A test for determining the inhibitory effects of the active substance of the invention was conducted in the following manner. To a solution of a mutagen in 0.02 ml of dimethyl sulfoxide was added 0.5 ml of the fraction obtained in each of the steps of the method shown in (1) above, or the final fraction (the active high-molecular-weight substance of the invention) obtained by the method shown in (1) above, and reacted at 37° C. for 30 minutes.

As a control, the above test procedure was followed except that 0.5 ml of a phosphate buffer was used instead of the fractions used in the above test.

In each run, the reaction mixture was then sterilized by heating at 100° C. for 10 minutes. After the heat-treatment, 3 ml of soft agar (0.6% Difco Agar) and 0.1 ml of a suspension of Salmonella TA98 (histidine requiring; His⁻) were added, and the mixture was poured onto a selection agar medium having the composition given hereinafter. The microorganism was then cultivated at 37° C. for 2 days, after which the colonies of revertants which did not require histidine (His+) were counted.

When the mutagen used was a substance manifesting mutagenicity only after being metabolized (such as 2-aminoanthracene, ethidium bromide, Trp-P-1 or Trp-P-2), the test was conducted in the same manner as above except that 0.3 ml of an S-9 mix prepared as described below was added to the soft agar. The S-9 mix was prepared by obtaining a liver homogenate having the activity of its drug metabolizing enzyme enhanced by PCB (polychrorinated biphenyl) from an SD-strain rat, centrifuging the liver homogenate to obtain a liver microsome fraction (S-9), and adding the following inorganic salts to the liver microsome.

| Inorganic salts added to S-9 | |
|---|---|
| Liver microsome | 3 ml |
| 0.25 M phosphate buffer | 4 ml |
| 0.16 M MgCl₂ | 0.5 ml |
| 0.66 M KCl | 0.5 ml |
| 0.05 M G-6-P | 1.0 ml |
| 0.04 NADP | 1.0 ml |
| Selection agar medium | |
| MM (X20) | 50 ml |
| 40% Glucose | 10 ml |
| 0.8% Difco nutrient broth | 10 ml |
| Biotin (100 μg/ml) | 1 ml |
| Agar | 15 g |
| Distilled water | 930 ml |
| Composition of MM (X20) used in the agar medium | |
| (NH₄)₂SO₄ | 2.0% |
| KH₂PO₄ | 20.0% |
| MgSO₄.7H₂O | 0.2% |
| Sodium citrate | 1.0% |
| pH: adjusted to 7.0 with KOH | |

The inhibitory effect of the high-molecular-weight substance of the invention was expressed by the amount (mg/plate) of the high-molecular-weight substance which was required to inhibit 50% of the mutagenicity of the mutagen which was determined by the same inhibitory effect test as above carried out by varying the concentration of the high-molecular-weight substance of the invention relative to the mutagen.

(b) Inhibitory effect on the mutagenicity of 2-nitro-o-phenylenediamine (80 μg/plate):

The concentration dependence of the dry powder (the active high-molecular-weight substance of the invention) on its desmutagenic effect is shown in Table 1.

TABLE 1

| Amount of 2-nitro-p-phenylenediamine (μg/plate) | Amount of an aqueous solution of dry powder (*1) (μl/plate) | Desmutagenic rate (*2) (%) |
|---|---|---|
| 80 | 500 | 87.4 |
| 80 | 300 | 85.1 |
| 80 | 100 | 79.4 |
| 80 | 10 | 22.3 |
| 80 | 0 | 0 |

(*1): The aqueous solution of dry powder is an aqueous solution of a lyophilized powder dissolved to a concentration of 12 mg/ml in a 50 mM phosphate buffer (pH 6.8).

(*2): Desmutagenic rate (%) = $\frac{a - b}{a - c} \times 100$ where a: Number of colonies of revertants in the absence of the high-molecular-weight substance,
b: Number of colonies of revertants in the presence of the lyophilized active high-molecular-weight substance of the invention,
c: Number of colonies of spontaneous revertants.

The foregoing results show that the high-molecular-weight substance of this invention had concentration dependence (Table 1), and exhibited a good inhibitory effect on the mutagenesis of 2-nitro-p-phenylenediamine.

Table 2 summarizes the inhibitory effects of the high-molecular-weight substance (final fraction) of the invention on the mutagenicity of various mutagens.

TABLE 2

| Mutagen | Concentration (μg/plate) | S-9 mix (added or not added) | Desmutagenic rate (%) |
|---|---|---|---|
| 2-nitro-p-phenylenediamine | 80 | not added | 89.9 |
| | 80 | added | 92.5 |
| 4-nitro-o-phenylenediamine | 40 | not added | 60.7 |
| | 40 | added | 56.9 |
| ethidium bromide | 10 | not added | 96.5 |
| | | added | |
| 2-amino-anthracene | 4 | not added | 97.8 |
| | | added | |
| Trp-P-1 | 0.2 | not added | 96.1 |
| | | added | |
| Trp-P-2 | 0.2 | not added | 95.5 |
| | | added | |

The results given in Table 2 demonstrate the especially outstanding inhibitory effect of the high-molecular-weight substance of the invention. The inhibitory factors present in the juices of cabbages and broccoli reported in the above-cited literature reference show inhibitory effects against those mutagens which manifest mutagenicity after going through metabolism (ethidium bromide, 2-aminoanthracene, Trp-P-1, Trp-P-2, etc.) but not on those mutagens which manifest mutagenicity without metabolism (e.g., some nitroaminobenzene-type dyes such as 2-nitro-p-phenylenediamine and 4-nitro-o-phenylenediamine). In contrast, the high-molecular-weight substance of this invention exhibits marked inhibitory effects as shown in Table 2 on both of these types of mutagens, and thus has marked specificity in action and effect.

(5) Heat resistance of the high-molecular-weight substance:

The final fraction (an aqueous solution of the lyophilized powder) of the invention was heat-treated at 100° C. for 15 minutes under reflux and cooled to room temperature. Five hundred microliters of each of the heat-treated fraction and the non-treated final fraction (aqueous solution) was mixed with each of the mutagens shown in Table 3 and reacted at 37° C. for 30 minutes in order to examine the heat resistance of the high-molecular-weight substance of the invention. The reaction product was tested for inhibitory effects in the same way as in (4) above. The results are shown in Table 3.

TABLE 3

| Mutagen | Concentration (μg/plate) | Final fraction (500 μl/plate | Desmutagenic rate (%) |
|---|---|---|---|
| 2-nitro-p-phenylenediamine | 200 | not heat-treated | 88.6 |
| | | heat-treated | 86.1 |
| 2-aminoanthracene | 4 | not heat-treated | 96.8 |
| | | heat-treated | 95.5 |
| ethidium bromide | 10 | not heat-treated | 95.5 |
| | | heat-treated | 93.5 |
| Trp-P-1 | 0.2 | not heat-treated | 96.8 |
| | | heat-treated | 96.2 |
| Trp-P-2 | 0.2 | not heat-treated | 95.8 |
| | | heat-treated | 96.0 |

The above results led to the determination that even when heated, the high-molecular-weight substance of this invention remains stable and is not deactivated, and exerts a good inhibitory effect.

(6) Stability of the active high-molecular-weight substance to polyvalent metal ion:

The stability of the high-molecular-weight substance (final fraction) of this invention to various polyvalent metal ions was examined as follows:

Each of magnesium chloride, manganese chloride and calcium chloride was dissolved in the high-molecular-weight substance (an aqueous solution of a lyophilized powder of the final fraction) of the invention so that the final concentration of each salt in the resulting solution reached 10 mM. The resulting solution was treated at 37° C. for 30 minutes.

Thereafter, 500 μl of the reaction mixture obtained was mixed with each of the mutagens shown in Table 4 in the concentrations indicated, and reacted at 37° C. for 30 minutes. After the reaction, the reaction mixture was subjected to the same inhibitory effect test as in (4) above.

The results are shown in Table 4.

TABLE 4

| Mutagen | Concentration (μg/plate) | Desmutagenic rate (%)* | | | |
|---|---|---|---|---|---|
| | | A | Mg++ | Mn++ | Ca++ |
| 2-nitro-p-phenylenediamine | 200 | 82.8 | 84.9 | 12.0 | 80.3 |
| 2-aminoanthracene | 4 | 95.2 | 94.1 | 8.5 | 90.1 |
| ethidium bromide | 10 | 93.8 | 92.1 | 10.2 | 94.1 |
| Trp-P-1 | 0.2 | 95.3 | 96.7 | 9.8 | 93.0 |

TABLE 4-continued

| Mutagen | Concentration (μg/plate) | Desmutagenic rate (%)* | | | |
|---|---|---|---|---|---|
| | | A | Mg++ | Mn++ | Ca++ |
| Trp-P-2 | 0.2 | 96.2 | 95.1 | 8.7 | 94.0 |

(*) Note
A: When the mutagen used was treated with the final fraction.
Mg++: When the mutagen used was treated with the final fraction treated with magnesium chloride.
Mn++: When the mutagen used was treated with the final fraction treated with manganese chloride.
Ca++: When the mutagen used was treated with the final fraction treated with calcium chloride.

The above results led to the determination that the final fraction of this invention is specific in that it is very stable to magnesium chloride and calcium chloride, but that its desmutagenic activity is drastically reduced by manganese chloride.

EXAMPLE 2

(1) Separation of the active high-molecular-weight substance from burdock and its purification:

Five thousand grams of the root of burdock harvested in spring was washed with water, and crushed by a juicer (Toshiba JC-540A, manufactured by Toshiba Co.) to obtain about 3400 ml of a burdock juice. The resulting juice (3400 ml) was centrifuged at 9000 G to give 2600 ml of a clear brown supernatant. The supernatant was mixed with a 1M phosphate buffer (pH 6.8) in an amount 1/20 the volume of the supernatant. The mixture (1500 ml) was then salted out with 80% by weight, based on the weight of the mixture, of ammonium sulfate. The salted-out mixture was centrifuged at 9000 G for 15 minutes to give 90 g of a precipitate. The precipitate (90 g) was dissolved in a 50 mM phosphate buffer (pH 6.8) to form 1000 ml of a solution. The solution was dialyzed at 4° C. against the above phosphate buffer (pH 6.8) by using a cellulose membrane to give 1162 ml of a dialyzate. A portion (962 ml) of the dialyzate was added to CM-Cellulose (manufactured by Watman Ltd, wet volume 500 g) equilibrated with a 50 mM phosphate buffer (pH 6.8), and the mixture was fully stirred at room temperature for 5 minutes, followed by filtration under reduced pressure. There was obtained 880 ml of a filtrate as a fraction not adsorbed to the CM-Cellulose. Then, 800 ml of the filtrate was ultrafiltered on a membrane filter-XM-300 (manufactured by Amicon Far East Ltd.) to concentrate it to ¼ of its original volume. A 50 mM phosphate buffer (pH 6.8) was added to the concentrate to form 800 ml of a mixture. The mixture was again ultrafiltered on the same filter as described above. This operation was further repeated. After the ultrafiltration, 200 ml of a concentrate (to be referred to as a final ultrafiltered solution) was obtained.

To a portion (130 ml) of the final ultrafiltered solution was gradually added trichloroacetic acid at room temperature with stirring so that the final concentration reached 2%. The solution was stirred at room temperature for 10 minutes, and the resulting precipitate was centrifuged at 9000 G for 15 minutes to give 4.5 g of a precipitate. The precipitate was again suspended in 130 ml of water, and then dialyzed against water to give about 160 ml of a dialyzate. The dialyzate was lyophilized at −54° C. for 48 hours by means of a lyophilizer (Model FDX-1-54 manufactured by Central Science Co., Ltd.) to give 730 mg of a dry powder (the high-molecular-weight substance of the invention).

(2) Ultraviolet absorbing characteristics of the active high-molecular-weight substance:

As in the active high-molecular-weight substance obtained in Example 1, the high-molecular-weight substance obtained in this Example had an absorption wavelength peak in the range of 280 nm to 300 nm (maximum wavelength about 290 nm).

(3) Adsorbability of the active high-molecular-weight substance to an anion exchange cellulose and a cation exchange cellulose:

As in Example 1, the active high-molecular-weight substance obtained in Example 2 had the property of being adsorbed to the anion exchange cellulose but not to the cation exchange cellulose.

(4) Inhibitory effect of the active high-molecular-weight substance (a) The inhibitory effect test was carried out in the same way as described in Example 1, (4), (a).

(b) Inhibitory effect on the mutagenesis of 2-nitro-p-phenylenediamine (200 μg/plate)

Table 5 shows the dry weight of each fraction required to inhibit 50% of mutagenicity, which was determined with respect to each of the fractions obtained by the steps of the method shown in (1) above.

TABLE 5

| Fraction | Dry weight (mg/plate) | Ratio |
|---|---|---|
| Supernatant obtained at 9000 G | 14.8 | 1 |
| Dialyzate | 7.1 | 2.1 |
| Final ultrafiltered solution | 2.0 | 7.4 |
| Aqueous solution of the dry powder | 1.0 | 14.8 |

Table 6 shows the concentration dependence of the dry powder (the active high-molecular-weight substance of the invention) which influences its desmutagenic effect.

TABLE 6

| Amount of 2-nitro-p-phenylenediamine (μg/plate) | Amount of an aqueous solution of the dry powder (μl/plate) (*1) | Desmutagenic rate (%) (*2) |
|---|---|---|
| 200 | 500 | 83 |
| 200 | 300 | 68 |
| 200 | 100 | 38 |
| 200 | 10 | 10 |
| 200 | 0 | 0 |

(*1): The aqueous solution of the dry powder was a solution obtained by dissolving the lyophilized powder in a 50 mM phosphate buffer (pH 6.8) to a concentration of 6 mg/ml.
(*2): The same as the footnote to Table 1.

The above results show that the desmutagenic activity of the high-molecular-weight substance of the invention (lyophilized powder) increased to about 15 times that of the supernatant obtained by centrifugation at 9000 G (control) and to about 2 times that of the salted-out dialyzate (see Table 5); that the final fraction obtained by this invention shows concentration dependence (see Table 6); and that it showed a good inhibitory effect on the mutagenicity of 2-nitro-p-phenylenediamine.

The inhibitory effects of the active high-molecular-weight substance (final fraction) of the invention on the mutagenicity of the various metagens shown in Table 2 were examined with or without the addition of the S-9 mix. The results obtained were similar to those given in Table 2.

(5) The heat resistance and stability of polyvalent metal ions of the active high-molecular-weight substance were tested and found to be the same as those of the active high-molecular-weight substance obtained in Example 1.

(6) Intrinsic viscosity of the active high-molecular-weight substance:

The final fraction was dissolved in a 1% aqueous solution of sodium hydroxide to a concentration of 1, 0.8, 0.5, and 0.25 mg/ml, respectively. 0.5 ml of each solution was taken, and its viscosity was determined by measuring the falling time at 25±0.1° C. by means of a Cannon-Manning semimicro-viscometer No. 100 (manufactured by Kaburagi Scientific Instruments Industry Co., Ltd.). As a control run, the falling time of a 1% aqueous solution of sodium hydroxide was measured. The results are shown in Table 7.

A line showing the relation between the reduced viscosity ($\eta_{sp/c}$) and the concentration (c) was determined by the least squares method from the viscosity values measured at the respective concentrations of the final fraction, and the intrinsic viscosity of the final fraction was determined to be 37.0 ml/g by extrapolation to the zero concentration.

TABLE 7

| Concentration (mg/ml) of the final fraction | $\eta_{sp/c}$(*) |
|---|---|
| 1 | 37.35 |
| 0.8 | 37.23 |
| 0.5 | 37.67 |
| 0.25 | 36.78 |

(7) Elemental analysis of the active high-molecular-weight substance:

The elemental analysis of the final fraction was carried out twice and the results are shown in Table 8. H, C and N were actually measured, and the other elements were calculated on the assumption that they were oxygen atoms.

TABLE 8

| Analysis | H (%) | C (%) | N (%) | O (%) |
|---|---|---|---|---|
| 1st | 4.72 | 48.29 | 5.93 | 41.06 |
| 2nd | 4.99 | 47.74 | 5.12 | 42.15 |
| Average | 4.86 | 48.02 | 5.53 | 41.61 |

(8) Carboxyl group of the active high-molecular-weight substance:

The $^{13}$C-NMR spectrum of the final fraction (solid) was measured by using tetramethylsilane (TMS) as an internal standard (instrument: JEOL FX-100 manufactured by JEOL, Ltd.; attachment, a cross-polarization/magic angle spinning (CP/MAS) unit).

Broad signals were observed in which maximum values existed at 173.68, 144.64, 127.97, 72.32 and 31.09 ppm (δ TMS). The $^{13}$C resonance frequency was 25.05 MHz and the contact time was 1.0 ms.

The signal at 173.68 shows the presence of the carboxyl group.

Twenty milligrams of the final fraction was dissolved in 20 ml of 0.01N NaOH (f=1,000; a product of Wako Pure Chemical Industries, Ltd.), and the solution was potentiometrically titrated (back-titrated) using 0.01N $H_2SO_4$ for volume analysis (f=1,000; a product of Wako Pure Chemical Industries, Ltd.). It was found that 13 ml of the 0.01N $H_2SO_4$ was required.

Assuming that the above titration value was derived only from the carboxyl group, the final fraction contained 3.5 eq/10³ g of carboxyl groups.

(9) Pyrolyzate of the active high-molecular-weight substance:

Three milligrams of the final fraction was pyrolyzed at 590° C. by means of a Curie point pyrolyzer (model JHP-2, manufactured by Japan Analysis Industry Co., Ltd.), and the pyrolyzate was analyzed by gas chromatography and mass spectrometry using instruments (JGC-20KP and JEOL-D300) manufactured by JEOL, Ltd.

The gas chromatography was carried out in a capillary column, 0.25 mm in diameter and 80 m in length, (a wall-coated open tubular capillary column made by Gas-Chro Industry Co., Ltd.) at a temperature elevating rate of 10° C./min, within the temperature range of 50° to 180° C. using FFAP (free fatty acid polyester) as a stationary phase liquid. The ionization voltage in the mass analysis was 70 eV (the same conditions were used hereinafter).

The results obtained led to the determination of the presence of $CO_2$, phenol, toluene, benzene, cresol and styrene as main components.

(10) Reductive decomposition of the active high-molecular-weight substance:

One gram of the final fraction and 4 g of Raney nickel were dissolved in 100 ml of a 4% aqueous solution of sodium hydroxide, and the solution was treated in an autoclave at 100° C. for 6 hours by introducing hydrogen gas under a pressure of 100 kg/cm¹ to decompose the final fraction reductively. After the reaction, the reaction mixture was allowed to cool to room temperature, and extracted with dichloromethane (for use in spectral analysis). The extract was analyzed by gas chromatography and mass spectrometry on the same instruments as described above.

The gas chromatrography was carried out in a capillary column, 0.25 mm in diameter and 50 m in length, (a wall-coated tubular capillary column made by Gas-Chro Industry Co., Ltd.) at a temperature elevating rate of 10° C./min. within the temperature range of 100° to 250° C. using Silicone SE-30 (a product of Wako Pure Chemical Industries, Ltd.) as a stationary phase liquid.

As a result, benzoic acid, phthalide and 3-phenyl-propanol were detected as main components.

(11) Oxidative decomposition of the active high-molecular-weight substance:

Five milliliters of a diazomethane ether solution was added to 500 mg of the final fraction, an reacted at room temperature for 30 minutes. After the reaction, the solid was collected by filtration, and washed with dichloromethane several times. The resulting solid was oxidatively decomposed with potassium premanganate in accordance with the method of S. Larson et al. [Acta. Chem. Scad., 25, 647 (1971)].

The decomposition product was extracted with a mixture of chloroform and acetone (1:1 by volume) and dried overnight on anhydrous sodium sulfate. The solvent was then removed, and the residue was dissolved in 0.5 ml of methanol. The methanol solution was subjected to the same gas chromatographic and mass spectrometric. instruments as described above to analyze the product. As a result, benzoic acid was detected.

The gas chromatography was performed in a packed column, 2.0 mm in diameter and 2 m in length, (Gas-Chrom Q, a packed column made by Applied Science Co., Ltd.) using 15% FFAP as a distribution agent at a temperature raising rate of 6° C./min. within the temperature range of 50° to 200° C.

(12) Sugar content of the active high-molecular-weight substance:

Ten milligrams of the lyophilized powder of the final fraction was dissolved under heat in 10 ml of a 50 mM phosphate buffer. The resulting aqueous solution was tested by the phenol/sulfuric acid method [M. Dubolis et al., Anal. Chem., 28, 350 (1956)] to determine its sugar content. It was found that each 1 ml portion of the solution contained 95.7 μg of sugar. Hence, the total sugar content of the lyophilized powder was calculated as 9.55% by weight.

(13) Ninhydrin color reaction of the active high-molecular-weight substance:

0.2 ml of 35% hydrochloric acid was added to 0.2 ml of a solution (1 mg/ml) of the lyophilized powder of the final fraction in a 50 mM phosphate buffer (pH 6.8), and the final fraction was hydrolyzed at 110° C. for 2 hours. The solvent was removed under reduced pressure at 50° C. to give a dried residue. The dried residue was dissolved in 1 ml of a 50 mM phosphate buffer (pH 6.8). The solution was developed on a silica gel thin layer (Wako Pure Chemicals Industries, Ltd.) using a mixture of n-propanol and water (64:36 by volume) as a developing solvent. Ninhydrin was added, but no component was found to react with it to form a color on the silica gel thin layer plate.

The ninhydrin color reaction is well known as a color reaction of an amino acid.

EXAMPLE 3

Six milligrams of the final fraction (lyophilized powder) obtained in Example 2, (1) was dissolved in 1 ml of a 50 mM phosphate buffer (pH 6.8). Using the resulting solution, the desmutagenic effect of the final fraction on the various mutagens shown in Table 9 was examined by the method described in Example 1, (4). The results are shown in Table 9.

For comparison, the supernatant obtained by centrifugation at 9000 G (in a concentration of 0.5 ml/plate) in Example 2, (1) was tested in the same way as above. The results are also shown in Table 9.

TABLE 9

| Mutagen | | | Number of colonies of revertants per plate | Desmutagenic rate (%) | |
|---|---|---|---|---|---|
| Type | Concentration (μg/plate) | Use of S-9 mix | | Final fraction | Supernatant at 9000 G |
| 2-Amino-4-nitrophenol | 500 | No | 168 | 79 | −667 (*) |
|  | 500 | Yes | 186 | 81 | −108 |
| 2-Amino-5-nitrophenol | 500 | No | 1437 | 75 | −2673 |
|  | 500 | Yes | 465 | 37 | −1485 |
| o-Phenylenediamine | 100 | Yes | 344 | 100 | 100 |
| p-Phenylene- | 100 | Yes | 1402 | 100 | 100 |

TABLE 9-continued

| Mutagen | | | Number of colonies of revertants per plate | Desmutagenic rate (%) | |
|---|---|---|---|---|---|
| Type | Concentration (μg/plate) | Use of S-9 mix | | Final fraction | Supernatant at 9000 G |
| diamine | | | | | |
| 2,4-Diaminoanisole sulfate | 100 | Yes | 658 | 100 | 100 |

(*): The - sign shows the promotion of mutation. For example, "−667%" means that the use of the supernatant promoted mutation to a degree more than 6 times as large as that obtained in the case of not using the supernatant.

The results give in Table 9 show that both the active high-molecular-weight substance and the supernatant at 9000 G inhibited the mutagenicity of o-phenylenediamine, p-phenylenediamine and 2,4-diaminoanisole which are mutagens manifesting mutagenicity upon metabolization, but that while the active high-molecular-weight substance of the invention inhibited the mutagenicity of 2-amino-4-nitrophenol and 2-amino-5-nitrophenol which are mutagens manifesting mutagenicity without metabolism, the supernatant at 9000 G markedly promoted their mutagenicity.

The foregoing results show that the high-molecular-weight substance of this invention is a polyelectrolyte having a strongly anionic group and an absorption wavelength in the range of 280 nm to 300 nm, has the property of being markedly reduced in desmutagenic activity by a manganese ion, and is stable to heat, and that it has high desmutagenic activity against many mutagens, especially those which manifest mutagenicity without being metabolized.

Although the entire structure of the high-molecular-weight substance of this invention has been unknown as yet, the foregoing analytical results show that it comprises carbon, hydrogen, nitrogen and oxygen and has a benzene ring, a carbohydrate structure and a carboxyl group.

What we claim is:

1. A process for producing a high-molecular-weight substance extracted from the root of edible burdock *Arctium Lappa Linne* or *Lappa edulis* SIEB belonging to the genus Arctium of the family Compositae, which comprises the steps of:
   (a) centrifuging an effective amount of juice squeezed from the root of said edible burdock to remove foreign materials therefrom,
   (b) mixing the resulting supernatant with a phosphate buffer in an amount of 1/20 to 1/100 the volume of said supernatant, said phosphate buffer consisting of monosodium or monopotassium phosphate and disodium or dipotassium phosphate as phosphates, and having a concentration of 1 to 2 moles and a pH of about 6.5 to about 7.5; salting out the resulting mixture with a water-soluble alkali metal or ammonium salt of an inorganic acid in an amount of about 30 to about 80% by weight based on said resulting mixture, said water-soluble alkali metal or ammonium salt of an inorganic acid being selected from the group consisting of potassium carbonate, ammonium sulfate, sodium sulfate and potassium phosphate; and thereafter collecting the resulting precipitate,
   (c) dissolving said precipitate in a phosphate buffer in an amount of about 5 to about 10 ml per gram of said precipitate; and dialyzing the resulting solution against water or a phosphate buffer, each of said phosphate buffers consisting of monosodium or monopotassium phosphate and disodium or dipotassium phosphate as phosphates, and having a concentration of about 10 to about 400 mM and a pH of about 6.5 to about 7.5, and
   (d) ultrafiltering the resulting dialyzate to a volume of ⅓ to 1/5 the volume of said dialyzate and withdrawing the resulting concentrate, and as required, lyophilizing said concentrate to yield a powder.

2. The process of claim 1 wherein said dialyzate obtained in step (c) is treated with a cation exchanger before it is submitted to step (d), said cation exchanger being a cellulose or dextran type exchanger containing a carboxyl group, a sulfonic acid group or a phosphoric acid group as cation exchange group.

3. The process of claim 1 wherein said concentrate obtained by ultrafiltration in step (d) is treated with trichloroacetic acid in a proportion of 1 to 10 g per 100 cc of said concentrate to form a precipitate; and the resulting precipitate is dialyzed against water.

4. The process of claim 1 or 2 wherein said concentrate obtained by ultrafiltration in step (d) is diluted with a phosphate buffer to the volume of the dialyzate prior to step (d), said phosphate buffer consisting of monosodium or monopotassium phosphate and disodium or dipotassium phosphate as phosphates, and having a concentration of about 10 to about 400 mM and a pH of about 6.5 to about 7.5; ultrafiltered again; and then dialyzed against water.

5. The product prepared by the process of claim 1.

6. A pharmaceutical composition comprising a therapeutically effective amount of said high-molecular-weight substance of claim 5 and a pharmaceutically acceptable carrier.

* * * * *